United States Patent
Nishida

(10) Patent No.: US 10,275,546 B2
(45) Date of Patent: Apr. 30, 2019

(54) METHOD OF PREDICTING CRACK GROWTH AND INFORMATION PROCESSING DEVICE THEREFOR

(75) Inventor: Hidetaka Nishida, Hiroshima (JP)

(73) Assignee: THE CHUGOKU ELECTRIC POWER CO., INC., Hiroshima (JP)

( * ) Notice: Subject to any disclaimer, the term of this patent is extended or adjusted under 35 U.S.C. 154(b) by 572 days.

(21) Appl. No.: 14/424,076

(22) PCT Filed: Aug. 31, 2012

(86) PCT No.: PCT/JP2012/072232
§ 371 (c)(1),
(2), (4) Date: Apr. 15, 2015

(87) PCT Pub. No.: WO2014/033927
PCT Pub. Date: Mar. 6, 2014

(65) Prior Publication Data
US 2015/0324697 A1 Nov. 12, 2015

(51) Int. Cl.
*G01R 31/26* (2014.01)
*G06F 17/50* (2006.01)
*G01M 5/00* (2006.01)

(52) U.S. Cl.
CPC ....... *G06F 17/5009* (2013.01); *G01M 5/0033* (2013.01); *G01N 2203/0062* (2013.01);
(Continued)

(58) Field of Classification Search
CPC .............. G01M 5/0033; G01N 29/043; G01N 29/4472
(Continued)

(56) References Cited

U.S. PATENT DOCUMENTS 8,109,150 B2 * 2/2012 Sato ........................ G01N 3/00
702/181
8,649,985 B2 * 2/2014 Dong .................. G06F 17/5009
702/34
(Continued)

FOREIGN PATENT DOCUMENTS

EP 2 172 761 A1 4/2010
JP 2006-105673 A 4/2006
(Continued)

OTHER PUBLICATIONS

A Study of Loading Path Influence on Fatigue Crack Growth under Combined Loading, Feng et al, Department of Mechanical Engineering 312, University of Nevada, Reno, Oct. 24, 2004, pp. 19-26.*
(Continued)

*Primary Examiner* — Calvin Lee
(74) *Attorney, Agent, or Firm* — Osha Liang LLP

(57) ABSTRACT

A method of predicting growth of a crack in a member includes memorizing, for each portion on the member, stress distribution Δσ(a) in the depth direction obtained in the case that no crack is present, a relationship between depth of growing cracks and creep contribution, and a relationship between creep contribution and parameters C and m of the Paris's law, receiving from a user an indication of a certain portion on the member, acquiring the stress distribution Δσ(a) in the depth direction for the certain portion, acquiring a creep contribution at the depth of a growing crack for the certain portion, from the relationship between depth of cracks and creep contribution memorized for the certain portion, and acquiring parameters C and m corresponding to the acquired creep contribution, from the relationship between creep contribution and parameters C and m of the Paris's law memorized for the certain portion.

24 Claims, 12 Drawing Sheets

(52) U.S. Cl.
CPC .. *G01N 2203/0066* (2013.01); *G06F 2217/16* (2013.01); *G06F 2217/80* (2013.01)

(58) Field of Classification Search
USPC ............ 702/35, 116, 185, 34, 181; 364/507; 438/14
See application file for complete search history.

(56) References Cited

U.S. PATENT DOCUMENTS

| | | | |
|---|---|---|---|
| 9,581,570 B2* | 2/2017 | Caicedo | G01N 29/043 702/39 |
| 2009/0281735 A1 | 11/2009 | Bechhoefer | |
| 2015/0324697 A1 | 11/2015 | Nishida | |

FOREIGN PATENT DOCUMENTS

| | | | |
|---|---|---|---|
| JP | 2007-256042 A | 10/2007 | |
| JP | 2008-003009 A | 1/2008 | |
| JP | 2009-031124 A | 2/2009 | |
| JP | 2010-216983 A | 9/2010 | |
| JP | 2011-095178 A | 5/2011 | |
| JP | 5567233 B1 | 8/2014 | |

OTHER PUBLICATIONS

Standard Practice for Statistical Analysis of Linear or Linearized Stress-Life and Strain-Life Fatigue Data, Designation: E 739-91 (Reapproved 2004), pp. 1-7.*
Office Action issued in corresponding Canadian Application No. 2,885,718 dated Mar. 13, 2017 (3 pages).
Office Action in counterpart Japanese Patent Application No. 2014-505434 dated Mar. 11, 2014 (6 pages).
Shibata Katsuyuki et al; "Development of a RPV Reliability Analysis Code Based on Probabilistic Fracture mechanics Methodology"; Journal of Nuclear Science and Technology, Japan; Atomic Energy Society of Japan; vol. 43, No. 4, pp. 387-396; Japan (14 pages).
Notification of Transmittal of Translation of the International Preliminary Report on Patentability in corresponding PCT Application No. PCT/JP2012/072232, dated Mar. 12, 2015. (1 page).
International Preliminary Report on Patentability in corresponding PCT Application No. PCT/JP2012/072232, dated Mar. 3, 2015. (1 page).
English translation of Written Opinion of the International Searching Authority issued in PCT/JP2012/072232 dated Nov. 27, 2012. (5 pages).
Extended European Search Report in counterpart European Application No. 12 883 660.8 dated Mar. 4, 2016 (8 pages).
Pugno et al; "A generalized Paris' law for fatigue crack growth"; Journal of the Mechanics and Physics of Solids, XP028050005, vol. 54, No. 7, pp. 1333-1349; Jul. 1, 2006 (17 pages).
Office Action in counterpart Korean Patent Application No. 10-2015-7005845 dated Apr. 11, 2017 (9 pages).
Office Action issued in corresponding Mexican Application No. MX/a/2015/002685 dated Jul. 27, 2016, and English translation thereof (4 pages).
Office Action in corresponding Chinese Patent Application No. 201280075936.X dated Mar. 29, 2016, with translation (7 pages).
Office Action in corresponding Chinese Patent Application No. 201280075936.X dated Oct. 24, 2016, with English translation (8 pages).
Office Action issued in corresponding Canadian Application No. 2,885,718 dated Jun. 22, 2016 (4 pages).
Office Action issued in corresponding Canadian Application No. 2,885,718 dated Mar. 22, 2018 (4 pages).
Office Action in corresponding Canadian Application No. 2,885,718 dated Feb. 8, 2019 (6 pages).

* cited by examiner

【Fig1】
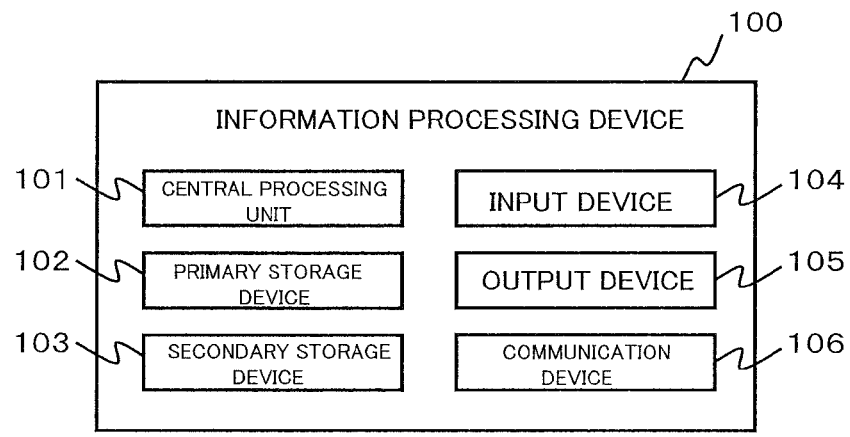
【Fig2】
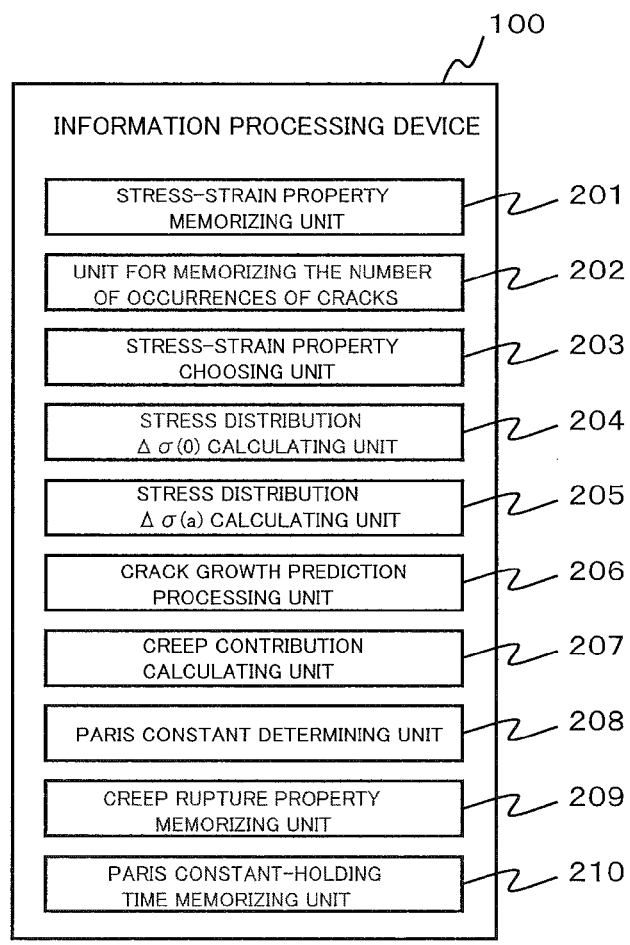

[Fig3]
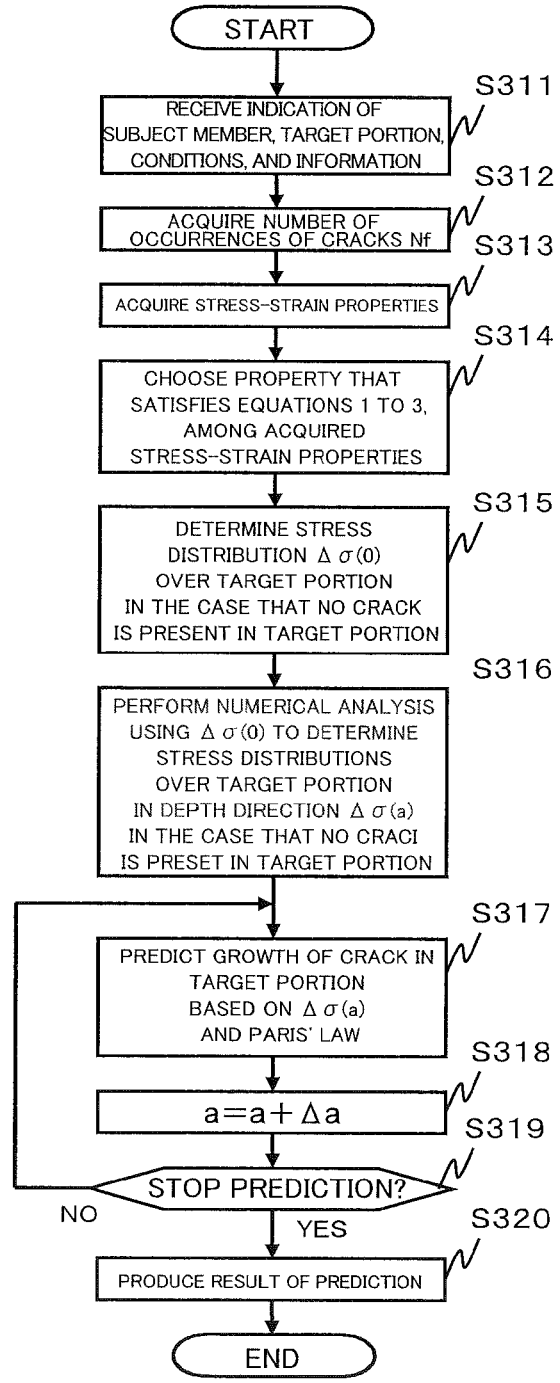

[Fig4]

| SETTINGS | INPUT WINDOW | UNIT | NOTES |
|---|---|---|---|
| MATERIAL | Cr-Mo-V CAST STEEL | — | ONLY Cr-Mo-V CAST STEEL IS AVAILABLE |
| STEAM TEMPERATURE | 540 | °C | |
| STEAM PRESSURE | 3 | MPa | |
| PORTION WHERE A CRACK APPEARS | NOTCH PORTION | — | CHOOSE FROM THE LIST |
| NUMBER OF SHUTDOWNS DUE TO OCCURRENCE OF CRACK | 617 | TIMES | |
| LENGTH OF CURRENT SURFACE CRACK | 20 | mm | |
| ASSUMED INITIAL CRACK DEPTH | 1 | mm | PREDICTED FROM LENGTH OF SURFACE CRACK WHEN INPUT IS OMITTED |
| $\Delta \sigma$, IF PROVIDED | 440 | MPa | USE STRAIN RANGE PARTITIONING WHEN INPUT IS OMITTED |

[Fig5]

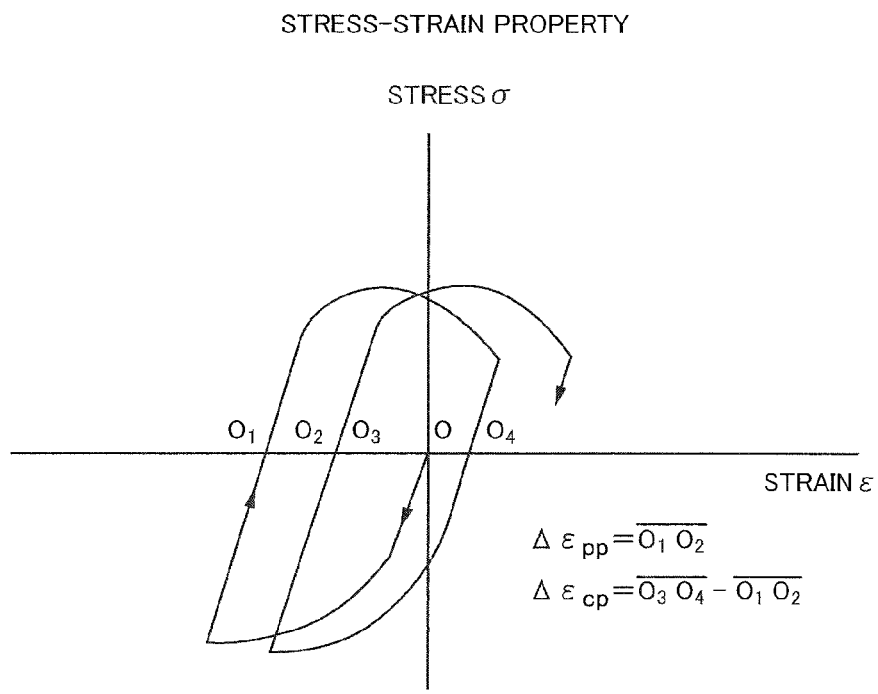

[Fig6]
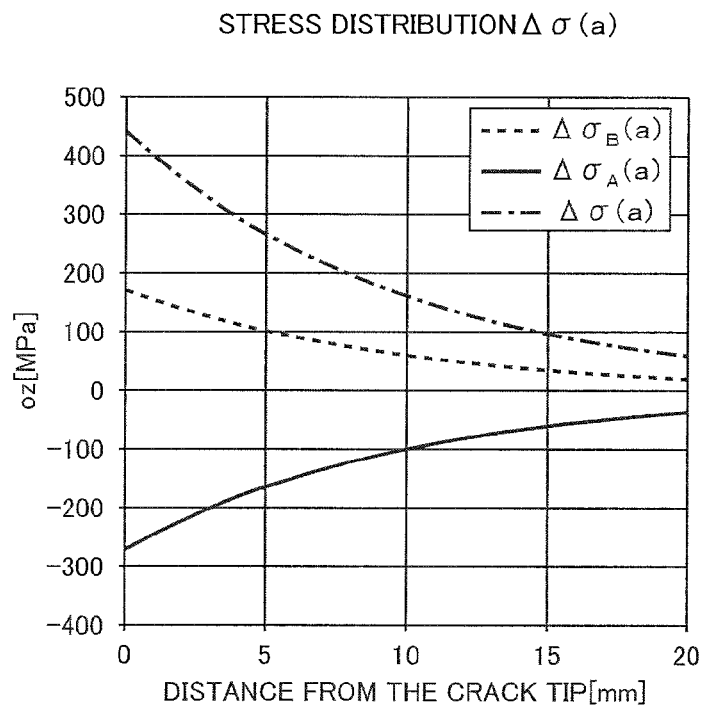
[Fig7]
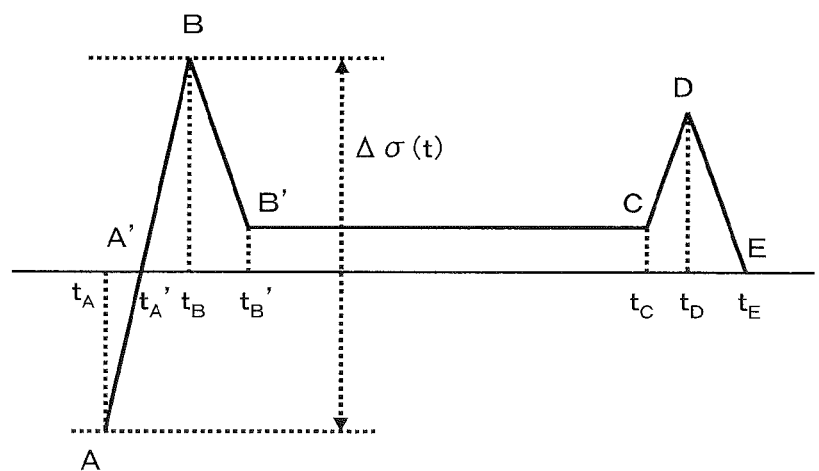

【Fig8】
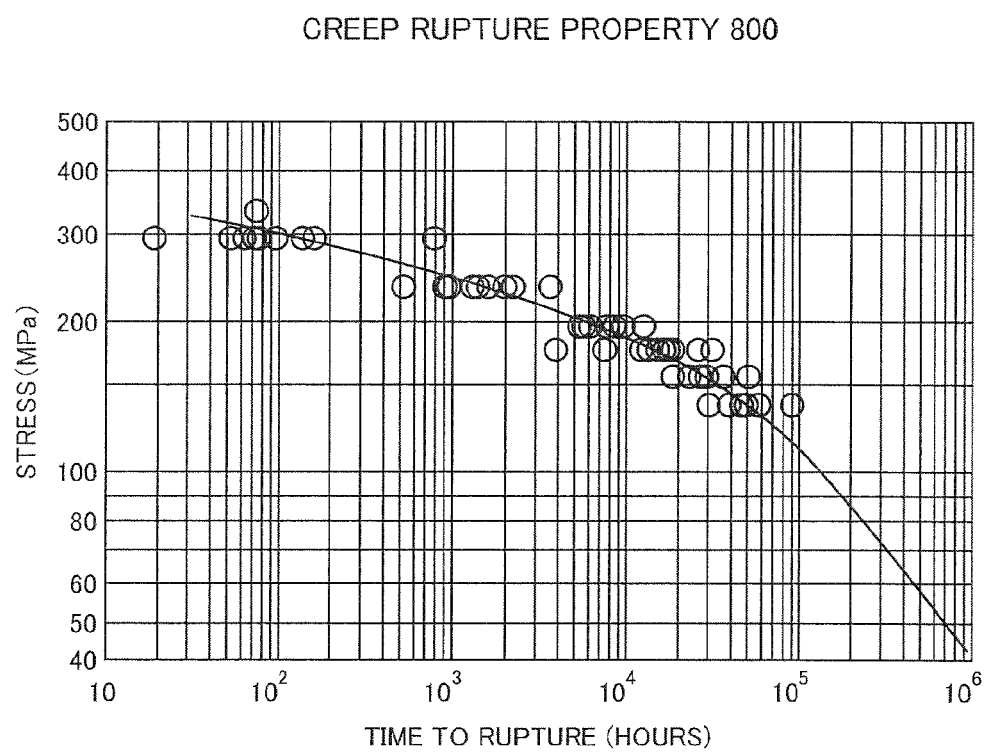

[Fig9]
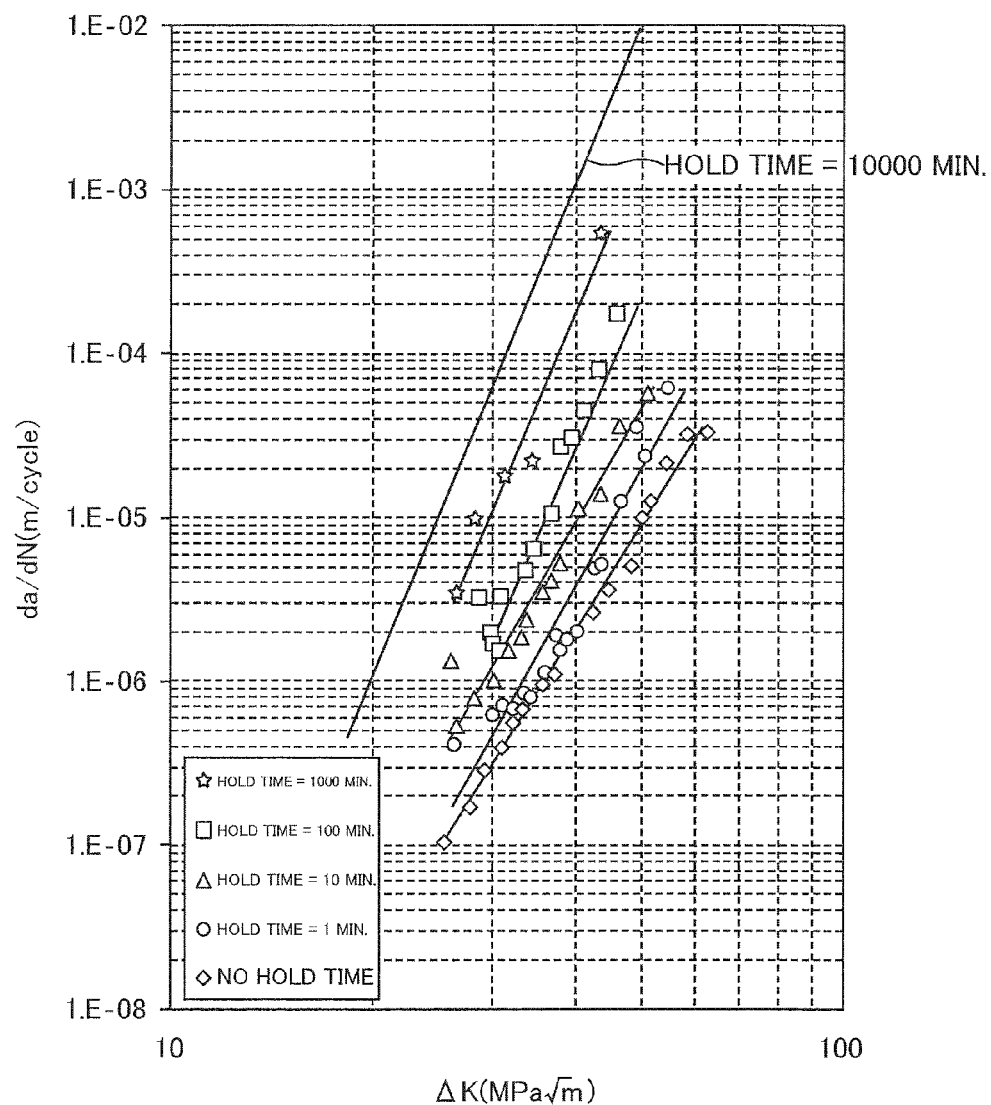

[Fig10]
| CRACK DEPTH | DATA TO BE USED |
|---|---|
| 1 mm < CRACK DEPTH < 3 mm | HOLD TIME: 10,000 MIN. |
| 3 mm < CRACK DEPTH < 5 mm | HOLD TIME: 1,000 MIN. |
| 5 mm < CRACK DEPTH < 20 mm | HOLD TIME: 100 MIN. |
[Fig11]
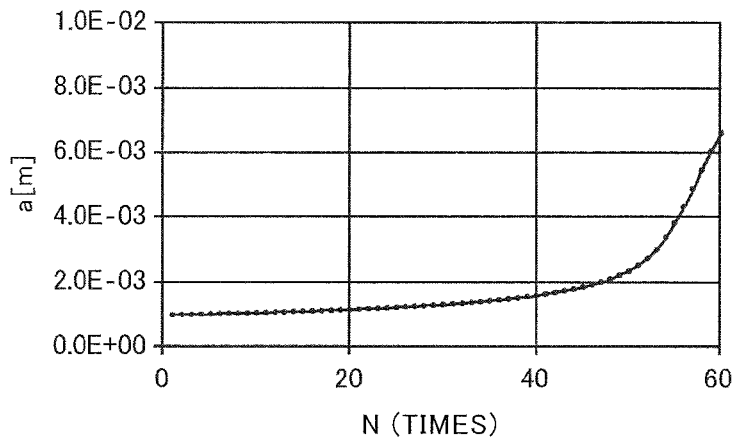
[Fig12]
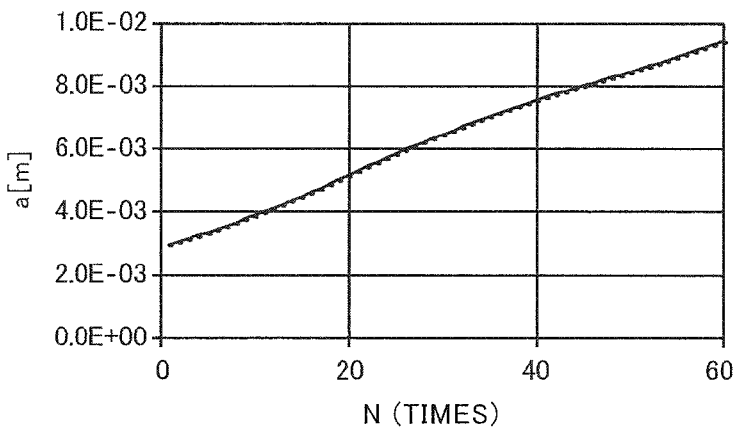

【Fig13】
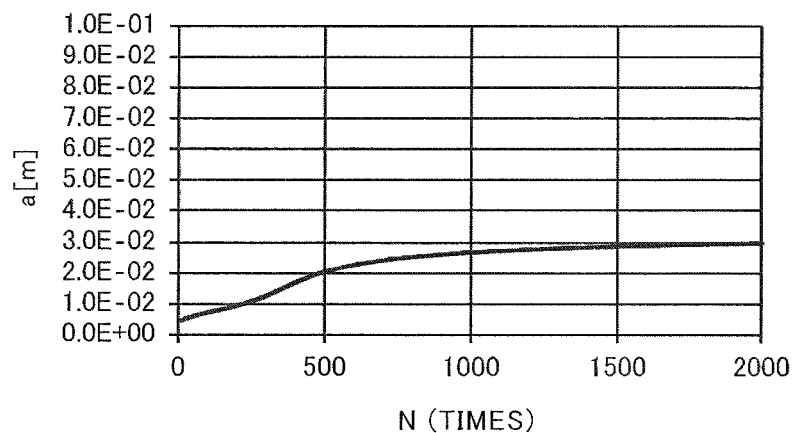
【Fig14】
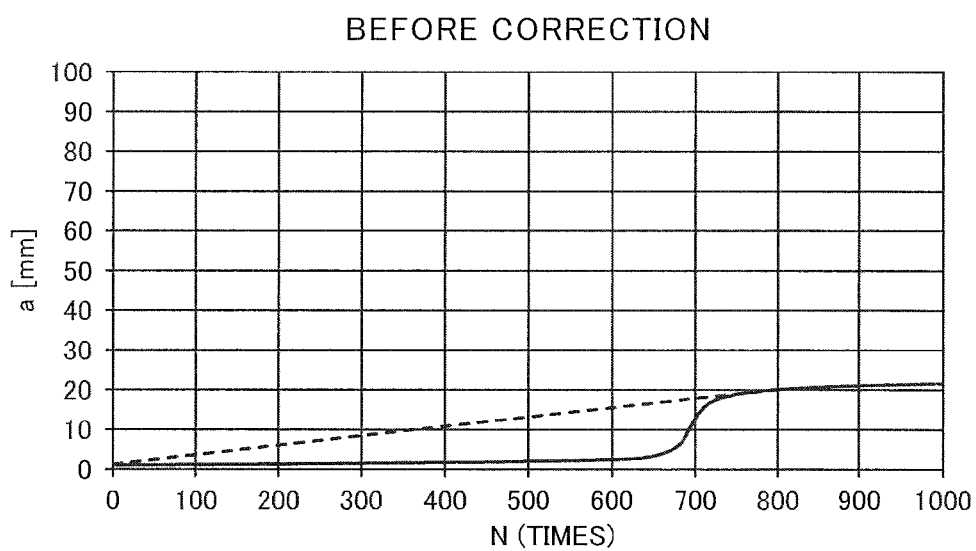

[Fig15]
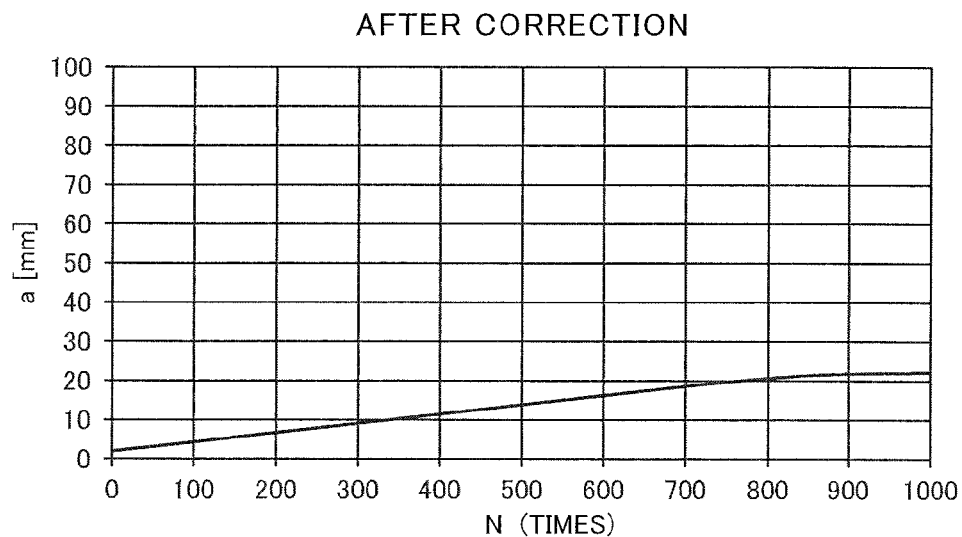
[Fig16]
| OPERATION CYCLES | ΔK (SIMPLIFIED METHOD) 151 | ΔK (SIMPLIFIED METHOD) 152 | ΔK (SIMPLIFIED METHOD) 153 | ΔJc (SOPHISTICATED METHOD) 154 |
|---|---|---|---|---|
| CONDITIONS | | WITHOUT PROVIDING SURFACE Δσ | WITHOUT PROVIDING SURFACE Δσ AND INITIAL CRACK DEPTH | |
| 1 TIME | 1.01 [mm] | 1.02 [mm] | 6.87 [mm] | 1.00 [mm] |
| 50 TIMES | 4.57 [mm] | 8.36 [mm] | 13.81 [mm] | 2.67 [mm] |
| 500 TIMES | 21.28 [mm] | 31.80 [mm] | 32.33 [mm] | 20.0 [mm] |
| 1000 TIMES | 27.11 [mm] | 35.14 [mm] | 35.32 [mm] | 20.0 [mm] |

[Fig17]

R PORTION

| DEPTH [m] | STRESS DISTRIBUTION [MPa] |
|---|---|
| 0.000 | 356.7 |
| 0.010 | 245.2 |
| 0.020 | 131.0 |
| 0.030 | 47.1 |
| 0.040 | 11.2 |
| 0.050 | 11.2 |
| 0.060 | 11.2 |
| 0.100 | 11.2 |
| 0.200 | 11.2 |
| 0.300 | 11.2 |
| 0.400 | 11.2 |
| 0.500 | 11.2 |
| 0.600 | 11.2 |
| 0.700 | 11.2 |
| 0.800 | 11.2 |
| 0.900 | 11.2 |
| 1.000 | 11.2 |
| 1.000 | 11.2 |

NOTCH PORTION

| DEPTH [m] | STRESS DISTRIBUTION [MPa] |
|---|---|
| 0.000 | 440.0 |
| 0.001 | 419.0 |
| 0.002 | 396.0 |
| 0.003 | 378.0 |
| 0.004 | 338.0 |
| 0.005 | 308.0 |
| 0.006 | 278.0 |
| 0.007 | 254.0 |
| 0.008 | 231.0 |
| 0.009 | 222.0 |
| 0.010 | 212.0 |
| 0.042 | 25.0 |
| 0.500 | 25.0 |
| 0.600 | 25.0 |
| 0.700 | 25.0 |
| 0.800 | 25.0 |
| 0.900 | 25.0 |
| 1.000 | 25.0 |

[Fig18]

| R PORTION | | NOTCH PORTION | |
|---|---|---|---|
| DEPTH [m] | CREEP CONTRIBUTION [%] | DEPTH [m] | CREEP CONTRIBUTION [%] |
| 0.000 | 10.40 | 0.000 | 17.00 |
| 0.005 | 7.25 | 0.001 | 17.00 |
| 0.010 | 5.06 | 0.003 | 17.00 |
| 0.015 | 3.43 | 0.004 | 17.00 |
| 0.020 | 2.32 | 0.005 | 17.00 |
| 0.025 | 1.06 | 0.006 | 3.70 |
| 0.030 | 0.48 | 0.007 | 3.70 |
| 0.035 | 0.48 | 0.008 | 3.70 |
| 0.040 | 0.48 | 0.009 | 3.70 |
| 0.045 | 0.48 | 0.010 | 3.70 |
| 0.050 | 0.48 | 0.012 | 1.40 |
| 0.500 | 0.48 | 0.014 | 1.40 |
| 0.600 | 0.48 | 0.016 | 1.40 |
| 0.700 | 0.48 | 0.018 | 1.40 |
| 0.800 | 0.48 | 0.020 | 1.40 |
| 0.900 | 0.48 | 0.022 | 1.40 |
| 1.000 | 0.48 | 0.024 | 1.40 |
| 1.000 | 0.43 | 0.500 | 1.40 |

[Fig19]

R PORTION

NOTCH PORTION

| CREEP CONTRIBUTION [%] | C | m | HOLD TIME (REFERENCE) [hour] | CREEP CONTRIBUTION [%] | C | m | HOLD TIME (REFERENCE) [hour] |
|---|---|---|---|---|---|---|---|
| 0.01 | 4.14E-18 | 7.46 | | 0.01 | 4.14E-18 | 7.46 | |
| 0.11 | 5.89E-18 | 7.46 | | 0.11 | 5.89E-18 | 7.46 | |
| 0.21 | 5.41E-18 | 7.58 | | 0.21 | 5.41E-18 | 7.58 | |
| 0.28 | 4.96E-18 | 7.71 | | 0.28 | 4.96E-18 | 7.71 | |
| 0.34 | 7.17E-17 | 6.97 | 10.0 | 0.34 | 7.17E-17 | 6.97 | 10.0 |
| 0.61 | 4.17E-18 | 7.95 | | 0.61 | 4.17E-18 | 7.95 | |
| 0.87 | 3.83E-18 | 8.07 | 31.6 | 0.87 | 3.83E-18 | 8.07 | 31.6 |
| 1.14 | 3.83E-18 | 8.07 | | 1.14 | 3.83E-18 | 8.07 | |
| 1.40 | 7.17E-22 | 10.50 | 100.0 | 1.40 | 7.17E-22 | 10.50 | 100.0 |
| 1.98 | 3.22E-18 | 8.32 | | 1.98 | 3.22E-18 | 8.32 | |
| 2.55 | 2.71E-18 | 8.56 | 316.2 | 2.55 | 2.71E-18 | 8.56 | 316.2 |
| 3.13 | 2.71E-18 | 8.56 | | 3.13 | 2.71E-18 | 8.56 | |
| 3.70 | 5.86E-20 | 9.69 | 1000.0 | 3.70 | 5.86E-20 | 9.69 | 1000.0 |
| 7.03 | 2.28E-18 | 8.81 | | 7.03 | 2.28E-18 | 8.81 | |
| 10.35 | 1.92E-18 | 9.05 | 3162.3 | 10.35 | 1.92E-18 | 9.05 | 3162.3 |
| 13.68 | 1.92E-18 | 9.05 | | 13.68 | 1.92E-18 | 9.05 | |
| 17.00 | 2.90E-18 | 9.02 | 10000.0 | 17.00 | 2.90E-18 | 9.02 | 10000.0 |
| 17.00 | 2.90E-18 | 9.02 | 10001.0 | 17.00 | 2.90E-18 | 9.02 | 10001.0 |

METHOD OF PREDICTING CRACK GROWTH AND INFORMATION PROCESSING DEVICE THEREFOR

TECHNICAL FIELD

Embodiments of the present invention relate to methods of predicting crack growth and information processing devices therefor and, more particularly, to techniques for accurately and easily predicting growth of a crack developing in a member.

BACKGROUND

Patent document 1 describes, in order to evaluate life of equipment subjected to creep fatigue damage, calculating plastic strain increments $\Delta\epsilon p$ based on strain that occurs under conditions where the load exerted on the equipment is fluctuating; calculating creep strain increments $\Delta\epsilon c$ based on increments of strain that occurs under conditions where the load exerted on the equipment is steady; calculating fatigue damage $\varphi p$ using the $\Delta\epsilon p$; calculating creep damage $\varphi c$ using the $\Delta\epsilon c$; and evaluating life of equipment.

Patent document 2 describes, in creep crack growth assessment, analyzing temperature and stress using input information and analysis data on temperature and stress in a database; analyzing creep crack growth life using the information obtained by the analysis, data of non-destructive inspection, and data obtained by the analysis of creep crack growth life; and judging the time to replace components for high-temperature apparatus from the information obtained by the analysis.

RELATED ART DOCUMENTS

Patent Documents

Patent document 1: Japanese Patent Laid-open No. 2010-216983
Patent document 2: Japanese Patent Laid-open No. 2008-3009

SUMMARY OF THE INVENTION

Analysis of cracks developing in structures used at high temperature, such as steam turbines and boilers in thermal or nuclear power plants, is typically made separately for initiation and growth of cracks. In many cases, a rule is made by which, if cracking is found in an apparatus in service in a field, the cracking portion is immediately removed, and behaviors of crack growth have not always been recognized.

Furthermore, an attempt for precise prediction of crack growth requires, for example, a numerical analysis using the finite element method (FEM). This is a labor-intensive process because meshes (FEM models) need to be re-meshed for each predicted depth of a growing crack and is also uneconomical because it is necessary to use a sophisticated information processing device.

One or more embodiments of the present invention provide methods of predicting crack growth with which growth of cracks developing in a member can accurately and easily be predicted, and information processing devices therefor.

One or more embodiments of the present invention are methods of predicting growth of a crack in a member comprising the steps, executed by an information processing device, of:

memorizing, for each portion on the member, stress distribution $\Delta\sigma(a)$ in the depth direction obtained in the case no crack is present, a relationship between depth of growing cracks and creep contribution, and a relationship between creep contribution and parameters C and m of the Paris's law;

receiving from a user an indication of a certain portion on the member;

acquiring the stress distribution $\Delta\sigma(a)$ in the depth direction for the certain portion;

acquiring a creep contribution at the depth of a growing crack for the certain portion, from the relationship between depth of cracks and creep contribution memorized for the certain portion;

acquiring parameters C and in corresponding to the acquired creep contribution, from the relationship between creep contribution and parameters C and m of the Paris's law memorized for the certain portion; and predicting the growth of the crack in the certain portion, based on the following equations:

$$da/dN = C \times (\Delta K)^m,$$

and $$\Delta K = \Delta\sigma(a) \times (\pi \times a)^{1/2}$$

wherein "a" is a crack depth, N is a number of occurrences of a cyclic stress, C and m are constants determined for a member, and $\Delta K$ is a stress intensity factor range.

According to one or more embodiments of the present invention, since growth of a crack is predicted by appropriately acquiring parameters C and m on the basis of the creep contribution at the depth of a growing crack, the growth of cracks developing in members can accurately and easily be predicted. In addition, the information processing device memorizes in advance, for each portion on members, the stress distribution $\Delta\sigma(a)$ in the depth direction in the case that no crack is present, the relationship between the depth of growing cracks and the creep contribution, and the relationship between the creep contribution and the parameters C and m of the Paris's law, and automatically acquires, for a portion on a member indicated by a user, the stress distribution $\Delta\sigma(a)$ in the depth direction, the creep contribution at the corresponding depth of the growing crack, and the parameters C and m corresponding to the creep contribution to predict the growth of the crack in the indicated portion. The user can thus easily and rapidly obtain accurate information about the growth of the crack in the indicated portion.

The information processing device calculates the relationship between the depth of cracks and the creep contribution based on, for example, temporal change of stress at a depth of a growing crack in the member, a creep rupture property, a measured value of a number of occurrences of a cyclic stress before a crack occurs in the member.

Since the relationship between the depth of cracks and the creep contribution is thus calculated based on the temporal change of the stress at the depth of a growing crack in the member, the growth of the crack can accurately be predicted in terms of the stress that varies at different depths of the growing crack in the member.

In addition, in the aforementioned method of predicting growth of a crack, the information processing device acquires, from the user, a length of the crack appeared on a surface of the certain portion; predicts a depth of the crack occurred in the certain portion based on the length of the crack; and defines the predicted depth of the crack as an initial value to be used in predicting a growth of a crack in the certain portion.

Thus, since the information processing device automatically predict the depth of a crack developing in a certain portion based on the length of the crack indicated by the user, the user can obtain information about the growth of the crack even when the user does not input the depth of the crack. The information processing device defines, for example, one third of the length of a surface crack as the crack depth in consideration of safety and a rule of thumb in the linear fracture mechanics.

In addition, in the aforementioned method of predicting growth of a crack, the information processing device corrects a curve representing the relationship between number N of the cyclic stresses and length "a" of a crack, the curve being obtained by predicting growth of cracks in the certain portion, in the case that the curve has a steeply changing segment where the length "a" of the crack steeply changes relative to the change in the number N of the cyclic stresses, by drawing a tangent line on an upwardly convex portion of the steeply changing segment from the vicinity of the origin. This allows us to obtain a good prediction result that is close to the one obtained using numerical computations (e.g., ΔJc).

One or more other embodiments of the present invention are methods of predicting growth of a crack wherein the stress distribution Δσ(a) in the depth direction obtained in the case no crack is present for each portion on the member is obtained by:

choosing, among known stress-strain properties, a property that satisfies the following equations:

$$1/N_f = 1/N_{pp} + 1/N_{cp},$$

$$\Delta\varepsilon_{cp} = A2 \times N_{cp}^{-\alpha 2},$$

and $$\Delta\varepsilon_{pp} = A1 \times N_{pp}^{-\alpha 1}$$

wherein $N_f$ is a known number of occurrences of cracks in the portion, $N_{cp}$ is a number of occurrences of cracks of a cp type (tensile creep strain+compressive plasticity strain) in strain range partitioning, $N_{pp}$ is a number of occurrences of cracks of a pp type (tensile plasticity strain+compressive plasticity strain) in the strain range partitioning, $\Delta\varepsilon_{cp}$ is a cp strain range in the strain range partitioning, $\Delta\varepsilon_{pp}$ is a pp strain range in the strain range partitioning, and A1, A2, α1, and α2 are all experimentally calculated constants; and determining stress distribution Δσ(0) of the portion in the case no crack is present in the portion based on the chosen stress-strain property to perform a numerical analysis based on the Δσ(0), and wherein:

by the information processing device the growth of the crack in the portion is predicted according to the acquired stress distribution Δσ(a) and the following equations:

$$da/dN = C \times (\Delta K)^m,$$

and $$\Delta K = \Delta\sigma(a) \times (\pi \times a)^{1/2}$$

wherein "a" is a crack depth, N is a number of occurrences of a cyclic stress, C and m are constants calculated for a member, and ΔK is a stress intensity factor range.

According to one or more embodiments of the present invention, a numerical analysis is performed only on a stress distribution Δσ(0) obtained in the case that no crack is present in the portion in which growth of a crack is to be predicted. The subsequent growth of the crack is then predicted using the Paris's law. Therefore, the growth of cracks can easily and rapidly be predicted without a considerable amount of numerical computations.

According to one or more embodiments of the present invention, since the parameters C and m are appropriately selected depending on the creep contribution at the depth of a growing crack to predict the growth of the crack using the Paris's law, accuracy of the crack growth prediction can be improved.

The information processing device memorizes, for example, the temporal changes of stress at the depths of the growing cracks in the member, the creep rupture properties, the measured values of the number of occurrences of the cyclic stress before the crack occurs in the portion and thereby calculates the creep contribution at the depth of a growing crack.

Furthermore, the information processing device memorizes, for example, relationships between the Paris constant and the hold time, identifies, among the relationship, the one whose creep contribution matches the calculated creep contribution at the depth of the growing crack, determines the parameters C and m based on the identified relationship, and predict the growth of the crack at the depth using the determined parameters C and m.

One or more alternative embodiments which are disclosed in the present application will be apparent from the description of the embodiments for carrying out the invention and drawings.

According to one or more embodiments of the present invention, growth of cracks developing in members can accurately and easily be predicted.

BRIEF DESCRIPTION OF THE DRAWINGS

FIG. 1 is a figure showing major hardware components of an information processing device 100 according to one or more embodiments.

FIG. 2 is a figure showing major functions of an information processing device 100 according to one or more embodiments.

FIG. 3 is a flowchart illustrating a crack growth prediction processing S300 according to one or more embodiments.

FIG. 4 shows a screen content which an information processing device 100 displays when receiving an information specified (or input) from a user according to one or more embodiments.

FIG. 5 is an example of the stress-strain property according to one or more embodiments.

FIG. 6 is an example of the stress distribution Δσ(a) in the target portion in the depth direction according to one or more embodiments.

FIG. 7 is an example of the temporal change of stress 700 at the depth of the growing crack according to one or more embodiments.

FIG. 8 is an example of the creep rupture property 800 according to one or more embodiments.

FIG. 9 is an example of the relationship between the Paris constant and the hold time 900 according to one or more embodiments.

FIG. 10 is a figure showing an example of the Paris constants C and m determined according to the creep contribution at the depth of the growing crack according to one or more embodiments.

FIG. 11 is an example of the result of the crack growth prediction according to one or more embodiments.

FIG. 12 is an example of the result of the crack growth prediction according to one or more embodiments.

FIG. 13 is an example of the result of the crack growth prediction according to one or more embodiments.

FIG. 14 is an example of the result of the crack growth prediction (before correction) according to one or more embodiments.

FIG. 15 is an example of the result of the crack growth prediction (after correction) according to one or more embodiments.

FIG. 16 is an example of the result of the crack growth prediction according to one or more embodiments.

FIG. 17 is an example of the stress distribution in the depth direction obtained in the case that no crack is present, which is memorized in an information processing device 100 according to one or more embodiments.

FIG. 18 is an example of the relationship between the depth of the growing crack and the creep contribution, which is memorized in the information processing device 100 according to one or more embodiments.

FIG. 19 is an example of relationships between the creep contribution and the Paris constants according to one or more embodiments, which is memorized in the information processing device 100.

DETAILED DESCRIPTION

Embodiments are described below with reference to the drawings.

FIG. 1 shows major hardware components of an information processing device 100 to be used for achieving a crack growth analysis system according to one or more embodiments. The crack growth analysis system of one or more embodiments is used in analysis or diagnosis of thermal cracks or fatigue cracks which appear in members of, for example, structures or various instruments used under high temperature conditions, such as a steam turbine or a boiler in a power plant (e.g., a thermal power plant or a nuclear power plant).

As shown in the figure, the information processing device 100 comprises a central processing unit 101 (e.g., a CPU or an MPU), a primary storage device 102 (e.g., ROM, RAM, and NVRAM), a secondary storage device 103 (e.g., a hard disk drive, a magneto-optical disk drive, or an SSD (Solid State Drive), an input device 104 (e.g., a keyboard, a mouse, or a touch panel), an output device 105 (e.g., a liquid crystal monitor or an organic EL panel), and a communication device 106 (e.g., a NIC (Network Interface Card)).

FIG. 2 shows major functions provided by the information processing device 100 according to one or more embodiments. As shown in the figure, the information processing device 100 provides functions of a stress-strain property memorizing unit 201, a unit for memorizing the number of occurrences of cracks 202, a stress-strain property choosing unit 203, a stress distribution $\Delta\sigma(0)$ calculating unit 204, a stress distribution $\Delta\sigma(a)$ calculating unit 205, a crack growth prediction processing unit 206, a creep contribution calculating unit 207, a Paris constant determining unit 208, a creep rupture property memorizing unit 209, and a Paris constant-hold time memorizing unit 210.

These functions are achieved by the central processing unit 101 loading and executing a program stored in the primary storage device 102 or the secondary storage device, or by a function of the hardware of the information processing device 100.

Among the functions shown in the figure, the stress-strain property memorizing unit 201 memorizes a plurality of stress-strain properties for respective stress ranges for one or more portions (predetermined positions on the aforementioned structure) on a member in which growth of a crack is to be predicted.

The unit for memorizing the number of occurrences of cracks 202 memorizes the number of occurrences of cracks, received through, for example, an input device 104, in each of one or more portions (such as an R portion, a notch portion, and an outer peripheral portion) on a member in which growth of a crack is to be predicted (such as a steam turbine and a boiler; hereinafter, referred to as a subject member).

The stress-strain property choosing unit 203 chooses a property that satisfies the following equations, among a plurality of stress-strain properties for respective stress ranges memorized in the stress-strain property memorizing unit 201 for a certain portion in which growth of a crack is to be predicted (hereinafter, referred to as a target portion) on a subject member:

$$1/N_f = 1/N_{pp} + 1/N_{cp} \quad \text{[equation 1]}$$

$$\Delta\varepsilon_{cp} = A2 \times N_{cp}^{-\alpha 2} \quad \text{[equation 2]}$$

and $$\Delta\varepsilon_{pp} = A1 \times N_{pp}^{-\alpha 1} \quad \text{[equation 3].}$$

$N_f$ is the number of occurrences of cracks in the target portion, $N_{cp}$ is the number of occurrences of cracks of a cp type (tensile creep strain+compressive plasticity strain) in strain range partitioning, $N_{pp}$ is the number of occurrences of cracks of a pp type (tensile plasticity strain+compressive plasticity strain) in the strain range partitioning, $\Delta\varepsilon_{cp}$ is a cp strain range in the strain range partitioning, $\Delta\varepsilon_{pp}$ is a pp strain range in the strain range partitioning, and A1, A2, α1, and α2 are all experimentally calculated constants (see, for example, Reference 1 "Masashi Nakashiro et al., "Failure analysis and metallurgical evaluation of turbine stop and control valves used at super high temperature and pressure plant", *Therm. Nucl. Power*, Vol. 35, No. 11, November 1984, p. 48").

The stress distribution $\Delta\sigma(0)$ calculating unit 204 calculates and memorizes a stress distribution $\Delta\sigma(0)$ (surface stress and a range of surface stress) in a target portion in the case that no crack is present in the target portion, based on a stress-strain property chosen by the stress-strain property choosing unit 203.

The stress distribution $\Delta\sigma(a)$ calculating unit 205 performs a numerical analysis (such as an analysis using the finite element method (FEM)) using the $\Delta\sigma(0)$ calculated by the stress distribution $\Delta\sigma(0)$ calculating unit 204 to calculate a stress distribution $\Delta\sigma(a)$ in a target portion in the depth direction in the case that no crack is present in the target portion (FIGS. 5 and 17).

The crack growth prediction processing unit 206 predicts growth of a crack in a target portion, based on a stress distribution $\Delta\sigma(a)$ calculated by the stress distribution $\Delta\sigma(a)$ calculating unit 205 and the following Paris's law equations:

$$da/dN = C \times (\Delta K)^m \quad \text{[equation 4],}$$

and $$\Delta K = \Delta\sigma(a) \times (\pi \times a)^{1/2} \quad \text{[equation 5].}$$

It is noted that "a" is a crack depth, N is the number of occurrences of a cyclic stress, C and m are constants determined for the subject member, and $\Delta K$ is a stress intensity factor range.

The creep contribution calculating unit 207 calculated relationships between depths of growing cracks and creep contributions (FIG. 18) on the aforementioned prediction performed by the crack growth prediction processing unit 206.

The Paris constant determining unit 208 determines Paris constants C and m which are used by the crack growth prediction processing unit 206 predicting growth of a growing crack at a depth of the crack, based on a relationship between the depth of the growing crack and a creep contribution (FIG. 18) calculated by the creep contribution calculating unit 207 and a relationships between the creep contribution and the Paris constants C and m (FIG. 19) described below.

The creep rupture property memorizing unit 209 memorizes a creep rupture property 700 (such as a creep rupture property experimentally obtained on the same material as a subject member) of the subject member which is described below (FIG. 6).

The Paris constant-hold time memorizing unit 210 memorizes relationships between Paris constants C and m and hold time 800 (FIG. 8).

FIG. 3 is a flowchart illustrating a processing of one or more embodiments (hereinafter, referred to as a crack growth prediction processing S300) executed by the information processing device 100 when a user uses the crack growth analysis system to predict growth of a crack. The crack growth prediction processing S300 is described below with reference to the figure.

First, the information processing device 100 receives, from a user through the input device 104, an indication of an object to be analyzed (such as a subject member, a target portion, or a material), operation conditions (such as a steam temperature and a steam pressure), and information about a crack (such as a state of crack occurrence) (S311).

FIG. 4 shows an example of one or more embodiments of a screen content which the information processing device 100 displays on the output device 105 upon the aforementioned input. As shown in the figure, in this example, the information processing device 100 receives quality of a material and a portion where a crack initiates as the object to be analyzed, a steam temperature and a steam pressure as operation conditions, and the number of shutdowns caused due to occurrence of a crack, the length of a current surface crack, and a crack depth (initial crack depth) as information on the crack.

With the screen content shown in FIG. 4, the user may skip indication (input) of the stress distribution $\Delta\sigma(0)$ in the target portion. When the user skips the indication of the stress distribution $\Delta\sigma(0)$, the information processing device 100 automatically calculates the stress distribution $\Delta\sigma(0)$ using strain range partitioning (which is a function of the aforementioned stress distribution $\Delta\sigma(0)$ calculating unit 204).

In addition, with the screen content shown in FIG. 4, the user may skip indication (input) of the crack depth (initial crack depth). In the case that the user skips the indication of the crack depth, the information processing device 100 calculates the crack depth from the length of the surface crack indicated (input). The information processing device defines, for example, one third of a surface crack as a crack depth in consideration of safety and a rule of thumb in the linear fracture mechanics.

Next, the information processing device 100 receives the number of occurrences of cracks $N_f$ and stress-strain properties for the respective stress ranges which are memorized for the indicated target portion (S312, S313).

FIG. 5 shows an example of the stress-strain properties (taken from Reference 1). The stress-strain property memorizing unit 201 memorizes a plurality of the stress-strain properties as shown in the figure for respective stress ranges.

Next, the information processing device 100 chooses a property that satisfies the aforementioned equations 1 to 3, among the received stress-strain properties for respective stress ranges (S314). The information processing device 100 then calculates a stress distribution $\Delta\sigma(0)$ in the target portion in the case that no crack is present in the target portion, based on the chosen stress-strain property (S315).

Next, the information processing device 100 performs a numerical analysis (such as an analysis using the finite element method (FEM)) using the calculated $\Delta\sigma(0)$ to calculate a stress distribution $\Delta\sigma(a)$ in the target portion in the depth direction in the case that no crack is present in the target portion (S316).

FIG. 6 shows an example of one or more embodiments of the aforementioned stress distribution $\Delta\sigma(a)$ calculated during this step. In this example, the $\Delta\sigma(a)$ is calculated based on the stress distribution along a straight line in the crack depth direction in the target portion, which is calculated using the aforementioned numerical analysis. In this example, a sum of the absolute value of a stress distribution $\Delta\sigma_A(a)$ at a time instant $(t_A)$ when compression reaches its maximum in the aforementioned numerical analysis and the absolute value of a stress distribution $\Delta\sigma_B(a)$ at a time instant $(t_B)$ when tension reaches its maximum in the aforementioned numerical analysis is calculated as the stress distribution $\Delta\sigma(a)$ in the target portion in the case that no crack is present in the target portion.

Turning back to FIG. 3, the information processing device 100 successively predicts the growth of the crack in the target portion (a relationship between number of occurrences of a cyclic stress N and crack depth), based on the calculated stress distributions $\Delta\sigma(a)$ and the aforementioned Paris's law (equations 3 and 4) (S317 to S319).

The shape of the subject member, the properties of a material and an environment (such as a temperature and a pressure) where the subject member is placed vary depending on the depth of a growing crack. Accordingly, in the aforementioned prediction, it is considered that the creep contribution also varies depending on the depth of a growing crack due to the action of a cyclic stress.

Specifically, when growth of a growing crack at each depth of the crack is predicted, the information processing device 100 calculates a creep contribution at the depth of the crack and determines (selects) Paris constants C and m according to the calculated creep contribution.

The creep contributions at the depths of a growing crack can be calculated by, for example, applying a temporal change of stress 700 at the depth of the growing crack, obtained by simplifying and simulating stress actually acting on the target portion (such as a stress acting on a given portion at start-up, during operation, and at stop of a steam turbine) as shown in FIG. 7 and a creep rupture property 800 illustrated in FIG. 8 (this figure is taken from Reference 2, that is, page 10 of NIMS CDS No. 31B 1994) to the equation given below:

$$\text{Creep contribution} = Nr \times \sum \frac{\Delta t}{tr(\Delta\sigma(t))} \qquad \text{[equation 6]}$$

where t is a time instant, and Nr is the number of occurrences of a cycle stress exerted before a crack occurs in the target portion, and $t_r(\Delta\sigma(t))$ is a time to rupture under the action of a stress $\Delta\sigma(t)$.

For example, for the surface of the target portion, the followings are herein assumed in the temporal change 700 in FIG. 7: $\Delta\sigma(t_B)=180$ MPa, $\Delta\sigma(t_C)=20$ MPa, and $\Delta\sigma(t_D)=140$ MPa; and $\Delta\sigma(t_B)$ of 180 MPa lasts for 3 hours from a time instant $t_A'$ to a time instant $t_B'$, $\Delta\sigma(t_C)$ of 20 MPa lasts for 150 hours from the time instant $t_B'$ to a time instant $t_C$, and $\Delta\sigma(t_D)$ of 140 MPa lasts for 3 hours from the time instant $t_C$ to a time instant $t_E$.

In this case, the following times can be received from the creep rupture property 800 in FIG. 8: 20,000 hours for the time to rupture corresponding to 180 MPa at the time instant $t_B$, 1.0E+07 (exponent notation) hours for the time to rupture corresponding to 20 MPa at the time instant $t_C$, and 50,000 hours for the time to rupture corresponding to 140 MPa at the time instant $t_D$. If the number of occurrences of a cyclic stress Nr is 617, then a creep contribution at that depth of the growing crack can be given from the equation 6 as:

$$\text{Creep contribution} = 617 \times \left( \frac{3}{20000} + \frac{150}{1.0E+07} - \frac{3}{50000} \right) = 13.9\%.$$

Further, for the portion where a crack has developed for 3 mm from the surface of the target portion, the followings are assumed in the temporal change 700 in FIG. 7: $\Delta\sigma(t_B)=140$ MPa, $\Delta\sigma(t_C)=15$ MPa, and $\Delta\sigma(t_D)=110$ MPa; and $\Delta\sigma(t_B)$ of 140 MPa lasts for 3 hours from the time instant $t_A'$ to the time instant $t_B'$, $\Delta\sigma(t_C)$ of 15 MPa lasts for 150 hours from the time instant $t_B'$ to the time instant $t_C$, and $\Delta\sigma(t_D)$ of 110 MPa lasts for 3 hours from the time instant $t_C$ to a time instant $t_E$.

In this case, the following times can be received from the creep rupture property 800 in FIG. 8: 4.0E+04 hours for the time to rupture corresponding to 140 MPa at the time instant $t_B$, 3.0E+07 hours for the time to rupture corresponding to 20 MPa at the time instant $t_C$, and 1.0E+05 hours for the time to rupture corresponding to 110 MPa at the time instant $t_D$. If the number of occurrences of a cyclic stress Nr is 617, then a creep contribution at the depth of the growing crack can be given from the equation 6 as:

$$\text{Creep contribution} = 617 \times \left( \frac{3}{4.0E+04} + \frac{150}{3.0E+07} - \frac{3}{1.0E+05} \right) = 6.8\%.$$

Further, for the portion where a crack has developed for 5 mm from the surface of the target portion, the followings are assumed in the temporal change 700 in FIG. 7: $\Delta\sigma(t_B)=100$ MPa, $\Delta\sigma(t_C)=10$ MPa, and $\Delta\sigma(t_D)=80$ MPa; and $\Delta\sigma(t_B)$ of 100 MPa lasts for 3 hours from the time instant $t_A'$ to the time instant $t_B'$, $\Delta\sigma(t_C)$ of 10 MPa lasts for 150 hours from the time instant $t_B'$ to the time instant $t_C$, and $\Delta\sigma(t_D)$ of 80 MPa lasts for 3 hours from the time instant $t_C$ to the time instant $t_E$.

In this case, the following times can be received from the creep rupture property 800 in FIG. 8: 1.5E+05 hours for the time to rupture corresponding to 100 MPa at the time instant $t_B$, 1.0E+08 hours for the time to rupture corresponding to 10 MPa at the time instant $t_C$, and 2.5E+05 hours for the time to rupture corresponding to 80 MPa at the time instant $t_D$. If Nr is 617, then a creep contribution at the depth of the growing crack can be given from the equation 6 as:

$$\text{Creep contribution} = 617 \times \left( \frac{3}{1.5E+05} + \frac{150}{1.0E+08} - \frac{3}{2.5E+05} \right) = 2.1\%.$$

Further, for the portion where a crack has developed for 10 mm from the surface of the target portion, the followings are assumed in the temporal change 700 in FIG. 7: $\Delta\sigma(t_B)=70$ MPa, $\Delta\sigma(t_C)=7$ MPa, and $\Delta\sigma(t_D)=56$ MPa; and $\Delta\sigma(t_B)$ of 70 MPa lasts for 3 hours from the time instant $t_A'$ to the time instant $t_B'$, $\Delta\sigma(t_C)$ of 7 MPa lasts for 150 hours from the time instant $t_B'$ to the time instant $t_C$, and $\Delta\sigma(t_D)$ of 56 MPa lasts for 3 hours from the time instant $t_C$ to the time instant $t_E$.

In this case, the following times can be received from the creep rupture property 800 in FIG. 8: 3.5E+05 hours for the time to rupture corresponding to 70 MPa at the time instant $t_B$, 3.0E+10 hours for the time to rupture corresponding to 10 MPa at the time instant $t_C$, and 6.0E+05 hours for the time to rupture corresponding to 80 MPa at the time instant $t_D$. If Nr is 617, then a creep contribution at the depth of the growing crack can be given from the equation 6 as:

$$\text{Creep contribution} = 617 \times \left( \frac{3}{3.5E+05} + \frac{150}{3.0E+10} - \frac{3}{6.0E+05} \right) = 0.84\%.$$

The information processing device 100 determines Paris constants C and m to be used for predicting the growth of the growing crack, according to the creep contribution at the depth of the crack thus calculated.

FIG. 9 shows an example of one or more embodiments of the relationship between the Paris constant and the hold time memorized in the information processing device 100. The data in this figure were obtained through actual measurements on specimens made of the same material (Cr—Mo—V cast steel) as an actual apparatus (such as a bent portion of a reheat stop valve in a steam turbine in a thermal power plant) in a predetermined environment (temperature: 550° C., stress: +220 MPa) except for the data for the hold time of 10,000 minutes. The data for the hold time of 10,000 minutes were estimated from the graphs for 1 to 1,000 minutes.

Creep contributions corresponding to each of the data (each line) shown in the figure can be calculated as follows. For example, it is assumed that the number of cyclic stresses which occurred up to the time when a specimen has been ruptured is 50 under conditions with a temperature of 550° C., a stress of 140 MPa, and a hold time of 167 hours. In this case, since 50,000 hours can be received, from the creep rupture property 800 in FIG. 8, for the time to rupture in the case of creep damage alone, a creep contribution with the hold time of 10,000 minutes can be given as:

Creep contribution (hold time: 10,000 min.)=50×(167/50000)=17%.

Further, for example, when it is assumed that the number of cyclic stresses which occurred up to the time when a specimen has been ruptured is 110 under conditions with a temperature of 550° C., a stress of 140 MPa, and a hold time of 16.7 hours, a creep contribution with the hold time of 1,000 minutes can be given as:

Creep contribution (hold time: 1,000 min.)=110×(16.7/50000)=3.7%.

Furthermore, for example, when it is assumed that the number of cyclic stresses which occurred up to the time when a specimen has been ruptured is 422 under conditions with a temperature of 550° C., a stress of 140 MPa, and a hold time of 1.67 hours, a creep contribution with the hold time of 100 minutes can be given as:

Creep contribution (hold time: 100 min.)=110×(1.67/50000)=1.4%.

In addition, for example, when it is assumed that the number of cyclic stresses which occurred up to the time when a specimen has been ruptured is 1025 under conditions with a temperature of 550° C., a stress of 140 MPa, and a hold time of 0.167 hours, a creep contribution with the hold time of 10 minutes can be given as:

Creep contribution (hold time: 10 min.)=1025×(0.167/50000)=0.34%.

When it is assumed that the number of cyclic stresses which occurred up to the time when a specimen has been ruptured is 2300 under conditions with a temperature of 550° C., a stress of 140 MPa, and a hold time of 0.0167 hours, a creep contribution with the hold time of 1 minute can be given as:

Creep contribution (hold time: 1 min.)=2300×(0.0167/50000)=0.34%.

The information processing device 100 compares each of the creep contributions on the graph obtained as described above (FIG. 9) with the creep contribution obtained using the equation 6 to identify the data having a value corresponding to the creep contribution obtained using the equation 6, among the data shown in FIG. 9. In the aforementioned comparison, logarithmic interpolation is used, if necessary. The information processing device 100 determines (selects) the constants C and m obtained from the data thus identified, as the Paris constants to be used for predicting growth of a growing crack at the depth of the crack.

FIG. 10 shows an example of one or more embodiments of the Paris constants C and m determined according to the creep contribution at a depth of a growing crack. This figure corresponds to a case in which: the Paris constants C and m corresponding to the data for the hold time of 10,000 minutes, 1,000 minutes, and 100 minutes is determined as the Paris constants to be used when the crack depth is equal to or more than 1 mm and less than 3 mm, equal to or more than 4 mm and less than 5 mm and equal to or more than 5 mm and less than 20 mm, respectively, in predicting growth of a growing crack at each depth of the crack.

Turning back to FIG. 3, the information processing device 100 outputs, upon completion of the prediction of the crack growth (S319: YES), the result thereof to the output device 105 (S320). For example, the information processing device 100 stops the prediction of the crack growth when the number of occurrences of a cyclic stress N exceeds a predetermined value.

FIGS. 11 to 13 show examples of one or more embodiments of results of the crack growth prediction output by the information processing device 100.

FIG. 11 shows one or more embodiments of a result of prediction of the growth of a crack whose depth is equal to or more than 1 mm and equal to or less than 3 mm (accuracy is not ensured in a range over 3 mm) using the Paris constants C and m corresponding to the data for the hold time of 10,000 minutes. It can be seen from the figure, for example, that the crack depth reaches 3 mm (3.0E-03m) when the cyclic stress occurs 50 times.

FIG. 12 shows one or more embodiments of a result of prediction of the growth of a crack whose depth is equal to or more than 3 mm and equal to or less than 5 mm (accuracy is not ensured in a range below 3 mm and over 5 mm) using the Paris constants C and m corresponding to the data for the hold time of 1,000 minutes. It can be seen from the figure, for example, that the crack depth reaches 5 mm (5.0E-03m) when the cyclic stress occurs 19 times after the depth of the crack exceeds 3 mm.

FIG. 13 shows one or more embodiments of a result of prediction of the growth of a crack whose depth is equal to or more than 5 mm and equal to or less than 20 mm (accuracy is not ensured in a range below 5 mm and over 20 mm) using the Paris constants C and m corresponding to the data for the hold time of 100 minutes. It can be seen from the figure, for example, that the crack depth reaches 20.9 mm (20.9E-03m) when the cyclic stress occurs 500 times after the depth of the crack exceeds 5 mm. In addition, from the same figure, the growth of the crack stops at or around the crack depth of 30.0 mm (30.0E-03m).

When growth of a crack is predicted according to the aforementioned method, a crack growth curve may steeply change (with a rate of change of a slope of a tangent line to the growth curve exceeding a predetermined amount) as shown in FIG. 14 (in this figure, the crack rapidly changes (grows) in a range of N=600 to 800). Such a rapid growth of a crack is not observed on cracks which are actually present in an actual component. It is believed that this should be due to application of a linear model to a non-linear event (growth of a crack according to the Paris's law is proportional to the eighth to tenth power of ΔK, whereas no such result cannot be found for an event in which a creep involves).

When a crack growth curve has such a steeply changing segment, the information processing device 100 draws a tangent line on an upwardly convex portion of the steeply changing segment of the curve from the origin. This tangent line (a line connecting between a point near the origin (the origin or a point near the origin) and a tangent point (a broken line in FIG. 14)) is used as a growth curve in place of the original growth curve. For example, when the growth curve as shown in FIG. 14 is obtained, the information processing device 100 corrects this into a growth curve as shown in FIG. 15. With such correction, a growth curve generally reflecting actual growth of cracks (or results of numerical computation of, for example, ΔJ) can be obtained.

As described above, in the crack growth analysis system according to one or more embodiments, a numerical analysis is performed only on a stress distribution Δσ(0) obtained in the case no crack is present in the portion in which growth of a crack is to be predicted, and the subsequent growth of the crack is predicted using the Paris's law. The growth of cracks can thus easily and rapidly be predicted using the information processing device 100 such as a personal computer.

In maintenance of cracks in structures used at high temperature, such as turbines and boilers in thermal or nuclear power plants, a rule is made in many cases, by which a crack is immediately repaired when it occurs. According to the crack growth analysis system of one or more embodiments, in the case that a crack occurs, subsequent growth of the crack can easily be predicted. Therefore, a way of dealing with a crack when it occurs can be determined (such as whether immediate repair is required) and maintenance of cracks in structures can be efficiently made.

Furthermore, in the crack growth analysis system according to one or more embodiments, the parameters C and in are appropriately selected on the basis of the creep contribution at the depth of a growing crack to predict the growth of the crack. Accordingly, the growth of cracks can be predicted with high accuracy. Moreover, the Paris constants C and m are considered as a function of time, i.e., C(t) and m(t), and the creep contribution and the hold time are connected to determine the Paris constants C and m to be used for the depth of a growing crack. Accordingly, the growth of cracks can be easily and accurately predicted using the relationship between the actually measured Paris constants C and m and the hold time (relationship between $\Delta K$ and da/dN). It is possible to enlarge a range in which crack growth can be predicted by predicting a relationship for the other hold time between the Paris constants C and m and the hold time, based on the relationship between the actually measured Paris constants C and m and the hold time.

Moreover, in the crack growth analysis system according to one or more embodiments, the information processing device 100 calculates the relationship between the depth of growing cracks and the creep contribution based on temporal change of stress at the depth of a growing crack, simplified stress actually acting on a member. Accordingly, the temporal change of stress actually acting on the member can be reflected to a calculation result, and the relationships between the depth of a growing crack and creep contribution can be calculated in a manner close to the reality. In addition, since stress actually acting on a member is simplified and temporal change of that stress at the depth of a growing crack is simulated, the relationship between the depth of a growing crack and the creep contribution can be more easily and rapidly calculated compared to the case where complicated stress actually acting on the member is taken into consideration.

As described above, the information processing device 100 automatically calculates stress distribution $\Delta\sigma(0)$ using strain range partitioning when a user does not indicate the stress distribution $\Delta\sigma(0)$. The information processing device 100 also calculates the depth of a crack from the length of the indicated surface crack in the case that the user does not indicate the depth of the crack.

FIG. 16 shows results of the crack growth prediction in accordance with one or more embodiments for cases where a user: indicates both of the stress distribution $\Delta\sigma(0)$ and the crack depth (reference numeral 151); does not indicate the stress distribution $\Delta\sigma(0)$ but indicates the crack depth (reference numeral 152), and indicates neither the stress distribution $\Delta\sigma(0)$ nor the crack depth (reference numeral 153), along with a case where numerical computation ($\Delta Jc$) is used (reference numeral 154). As shown in the figure, even when the user does not indicate stress distribution $\Delta\sigma(0)$ and/or crack depth, growth of a crack can be predicted with high accuracy.

The embodiments described above are for the purpose of facilitating the understanding of the present invention and do not limit the present invention. It is needless to say that the present invention can be modified or improved without departing from spirit thereof and encompasses equivalents thereof.

For example, the information processing device 100 may calculate and memorize (as a database) in advance, for each target portion (such as an R portion, a notch portion, or an outer peripheral portion), the stress distribution $\Delta\sigma(a)$ in the depth direction in the case that no crack is present (FIG. 6), the relationship between the depth of a growing crack and the creep contribution (which can be calculated with the equation 6) and the relationship between the creep contribution and the Paris constants C and m; thereby a user can obtain results of crack growth prediction more easily and rapidly.

In this case, an example of stress distributions in the depth direction obtained in the case that no crack is present, an example of the relationship between the depth of a growing crack and the creep contribution, and an example of the relationship between the creep contribution and the Paris constants C and m, which are memorized in the information processing device 100, are shown in FIGS. 17, 18, and 19, respectively.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

DENOTATION OF REFERENCE NUMERALS 100 information processing device
201 stress-strain property memorizing unit
202 a unit for memorizing the number of occurrences of cracks
203 stress-strain property choosing unit
204 stress distribution $\Delta\sigma(0)$ calculating unit
205 stress distribution $\Delta\sigma(a)$ calculating unit
206 crack growth prediction processing unit
207 creep contribution calculating unit
208 Paris's law parameter selection unit
209 creep rupture property memorizing unit
210 Paris constant-hold time memorizing unit
S300 crack growth prediction processing
500 temporal change of stress at depths of a growing crack
600 creep rupture property
700 relationship between Paris constants and hold time

The invention claimed is:

1. A method of predicting growth of a crack in a member, the method executed by an information processing device and comprising:

storing in a memory of the information processing device, for each portion on the member, stress distribution $\Delta\sigma(a)$ in the depth direction obtained in the case that no crack is present, a first relationship between depth of growing cracks and creep contribution, and a second relationship between creep contribution and parameters C and m of the Paris's law;

receiving, with a receiver of the information processing device, from a user an indication of a certain portion on the member;

determining, with a central processing unit (CPU) of the information processing device connected to the memory and the receiver, the stress distribution $\Delta\sigma(a)$ in the depth direction for the certain portion;

determining, with the CPU, a creep contribution at the depth of a growing crack for the certain portion, from the first relationship stored for the certain portion;

determining, with the CPU, parameters C and m corresponding to the determined creep contribution, from the second relationship stored for the certain portion; and predicting, with the CPU, the growth of the crack in the certain portion, based on the following equations:

$$da/dN = C \times (\Delta K)^m, \text{ and}$$

$$\Delta K = \Delta \sigma(a) \times (\pi \times a)^{1/2};$$

causing, with the CPU, a display to display the predicted the growth of the crack, wherein "a" is a crack depth, N is a number of occurrences of a cyclic stress, C and m are constants determined for a member, and $\Delta K$ is a stress intensity factor range.

2. The method according to claim 1, wherein the stress distribution $\Delta \sigma(a)$ in the depth direction obtained in the case that no crack is present for each portion on the member is obtained by:

choosing, among known stress-strain properties, a property that satisfies the following equations:

$$1/N_f = 1/N_{pp} + 1/N_{cp},$$

$$\Delta \varepsilon_{cp} = A2 \times N_{cp}^{-\alpha 2}, \text{ and}$$

$$\Delta \varepsilon_{pp} = A1 \times N_{pp}^{-\alpha 1}$$

wherein $N_f$ is a known number of occurrences of cracks in the portion, $N_{cp}$ is a number of occurrences of cracks of a cp type (tensile creep strain+compressive plasticity strain) in strain range partitioning, $N_{pp}$ is a number of occurrences of cracks of a pp type (tensile plasticity strain+compressive plasticity strain) in the strain range partitioning, $\Delta \varepsilon_{cp}$ is a cp strain range in the strain range partitioning, $\Delta \varepsilon_{pp}$ is a pp strain range in the strain range partitioning, and A1, A2, $\alpha 1$, and $\alpha 2$ are all experimentally calculated constants; and determining stress distribution $\Delta \sigma(0)$ of the portion in the case that no crack is present in the portion based on the chosen stress-strain property to perform a numerical analysis based on the $\Delta \sigma(0)$, and wherein:

by the information processing device the growth of the crack in the portion is predicted according to the acquired stress distribution $\Delta \sigma(a)$ and the following equations:

$$da/dN = C \times (\Delta K)^m, \text{ and}$$

$$\Delta K = \Delta \sigma(a) \times (\pi \times a)^{1/2}$$

wherein "a" is a crack depth, N is a number of occurrences of a cyclic stress, C and m are constants determined for a member, and $\Delta K$ is a stress intensity factor range.

3. The method according to claim 1, further comprising:
when a curve representing a third relationship between number N of the cyclic stresses and length "a" of a crack has a steeply changing segment where the length "a" of the crack steeply changes relative to the change in the number N of the cyclic stresses, correcting, with the CPU, the curve by drawing a tangent line on an upwardly convex portion of the steeply changing segment from the vicinity of the origin, wherein the curve is obtained by predicting growth of cracks in the certain portion.

4. The method according to claim 3, wherein the stress distribution $\Delta \sigma(a)$ in the depth direction obtained in the case that no crack is present for each portion on the member is obtained by:

choosing, among known stress-strain properties, a property that satisfies the following equations:

$$1/N_f = 1/N_{pp} + 1/N_{cp},$$

$$\Delta \varepsilon_{cp} = A2 \times N_{cp}^{-\alpha 2}, \text{ and}$$

$$\Delta \varepsilon_{pp} = A1 \times N_{pp}^{-\alpha 1}$$

wherein $N_f$ is a known number of occurrences of cracks in the portion, $N_{cp}$ is a number of occurrences of cracks of a cp type (tensile creep strain+compressive plasticity strain) in strain range partitioning, $N_{pp}$ is a number of occurrences of cracks of a pp type (tensile plasticity strain+compressive plasticity strain) in the strain range partitioning, $\Delta \varepsilon_{cp}$ is a cp strain range in the strain range partitioning, $\Delta \varepsilon_{pp}$ is a pp strain range in the strain range partitioning, and A1, A2, $\alpha 1$, and $\alpha 2$ are all experimentally calculated constants; and determining stress distribution $\Delta \sigma(0)$ of the portion in the case that no crack is present in the portion based on the chosen stress-strain property to perform a numerical analysis based on the $\Delta \sigma(0)$, and wherein:

by the information processing device the growth of the crack in the portion is predicted according to the acquired stress distribution $\Delta \sigma(a)$ and the following equations:

$$da/dN = C \times (\Delta K)^m, \text{ and}$$

$$\Delta K = \Delta \sigma(a) \times (\pi \times a)^{1/2}$$

wherein "a" is a crack depth, N is a number of occurrences of a cyclic stress, C and m are constants determined for a member, and $\Delta K$ is a stress intensity factor range.

5. The method according to claim 1, wherein the first relationship stored in the memory is calculated based on temporal change of stress at a depth of a growing crack in the member, a creep rupture property, a measured value of a number of occurrences of a cyclic stress before a crack occurs in a portion on the member.

6. The method according to claim 5, further comprising:
receiving, with the receiver, from the user, a length of the crack appeared on a surface of the certain portion; and
predicting, with the CPU, a depth of the crack occurred in the certain portion based on the length of the crack,
wherein the predicted depth of the crack is defined as an initial value to be used in predicting a growth of a crack in the certain portion.

7. The method according to claim 6, wherein by the information processing device a value obtained by multiplying the acquired length of the crack appeared on the surface of the certain portion with ⅓ is used as a predicted value for the depth of the crack occurred in the certain portion.

8. The method according to claim 1, comprising:
acquiring, from the user, a length of the crack appeared on a surface of the certain portion;
predicting a depth of the crack occurred in the certain portion based on the length of the crack; and
the predicted depth of the crack is defined as an initial value to be used in predicting a growth of a crack in the certain portion.

9. The method according to claim 8, wherein the stress distribution $\Delta \sigma(a)$ in the depth direction obtained in the case that no crack is present for each portion on the member is obtained by:

choosing, among known stress-strain properties, a property that satisfies the following equations:

$$1/N_f = 1/N_{pp} + 1/N_{cp},$$

$$\Delta \varepsilon_{cp} = A2 \times N_{cp}^{-\alpha 2}, \text{ and}$$

$$\Delta \varepsilon_{pp} = A1 \times N_{pp}^{-\alpha 1}$$

wherein $N_f$ is a known number of occurrences of cracks in the portion, $N_{cp}$ is a number of occurrences of cracks of a cp type (tensile creep strain+compressive plasticity strain) in strain range partitioning, $N_{pp}$ is a number of occurrences of cracks of a pp type (tensile plasticity strain+compressive plasticity strain) in the strain range partitioning, $\Delta\varepsilon_{cp}$ is a cp strain range in the strain range partitioning, $\Delta\varepsilon_{pp}$ is a pp strain range in the strain range partitioning, and A1, A2, α1, and α2 are all experimentally calculated constants; and determining stress distribution $\Delta\sigma(0)$ of the portion in the case that no crack is present in the portion based on the chosen stress-strain property to perform a numerical analysis based on the $\Delta\sigma(0)$, and wherein:

by the information processing device the growth of the crack in the portion is predicted according to the acquired stress distribution $\Delta\sigma(a)$ and the following equations:

$$da/dN = C \times (\Delta K)^m, \text{ and}$$

$$\Delta K = \Delta\sigma(a) \times (\pi \times a)^{1/2}$$

wherein "a" is a crack depth, N is a number of occurrences of a cyclic stress, C and m are constants determined for a member, and $\Delta K$ is a stress intensity factor range.

10. The method according to claim 8, wherein when a curve representing a third relationship between number N of the cyclic stresses and length "a" of a crack has a steeply changing segment where the length "a" of the crack steeply changes relative to the change in the number N of the cyclic stresses, the curve is corrected by drawing a tangent line on an upwardly convex portion of the steeply changing segment from the vicinity of the origin, and wherein the curve is obtained by predicting growth of cracks in the certain portion.

11. The method according to claim 10, wherein the stress distribution $\Delta\sigma(a)$ in the depth direction obtained in the case that no crack is present for each portion on the member is obtained by:

choosing, among known stress-strain properties, a property that satisfies the following equations:

$$1/N_f = 1/N_{pp} + 1/N_{cp},$$

$$\Delta\varepsilon_{cp} = A2 \times N_{cp}^{-\alpha 2}, \text{ and}$$

$$\Delta\varepsilon_{pp} = A1 \times N_{pp}^{-\alpha 1}$$

wherein $N_f$ is a known number of occurrences of cracks in the portion, $N_{cp}$ is a number of occurrences of cracks of a cp type (tensile creep strain+compressive plasticity strain) in strain range partitioning, $N_{pp}$ is a number of occurrences of cracks of a pp type (tensile plasticity strain+compressive plasticity strain) in the strain range partitioning, $\Delta\varepsilon_{cp}$ is a cp strain range in the strain range partitioning, $\Delta\varepsilon_{pp}$ is a pp strain range in the strain range partitioning, and A1, A2, α1, and α2 are all experimentally calculated constants; and determining stress distribution $\Delta\sigma(0)$ of the portion in the case that no crack is present in the portion based on the chosen stress-strain property to perform a numerical analysis based on the $\Delta\sigma(0)$, and wherein:

by the information processing device the growth of the crack in the portion is predicted according to the acquired stress distribution $\Delta\sigma(a)$ and the following equations:

$$da/dN = C \times (\Delta K)^m, \text{ and}$$

$$\Delta K = \Delta\sigma(a) \times (\pi \times a)^{1/2}$$

wherein "a" is a crack depth, N is a number of occurrences of a cyclic stress, C and m are constants determined for a member, and $\Delta K$ is a stress intensity factor range.

12. The method according to claim 8, wherein by the information processing device a value obtained by multiplying the acquired length of the crack appeared on the surface of the certain portion with ⅓ is used as a predicted value for the depth of the crack occurred in the certain portion.

13. The method according to claim 12, wherein the stress distribution $\Delta\sigma(a)$ in the depth direction obtained in the case that no crack is present for each portion on the member is obtained by:

choosing, among known stress-strain properties, a property that satisfies the following equations:

$$1/N_f = 1/N_{pp} + 1/N_{cp},$$

$$\Delta\varepsilon_{cp} = A2 \times N_{cp}^{-\alpha 2}, \text{ and}$$

$$\Delta\varepsilon_{pp} = A1 \times N_{pp}^{-\alpha 1}$$

wherein $N_f$ is a known number of occurrences of cracks in the portion, $N_{cp}$ is a number of occurrences of cracks of a cp type (tensile creep strain+compressive plasticity strain) in strain range partitioning, $N_{pp}$ is a number of occurrences of cracks of a pp type (tensile plasticity strain+compressive plasticity strain) in the strain range partitioning, $\Delta\varepsilon_p$ is a cp strain range in the strain range partitioning, $\Delta\varepsilon_{pp}$ is a pp strain range in the strain range partitioning, and A1, A2, α1, and α2 are all experimentally calculated constants; and determining stress distribution $\Delta\sigma(0)$ of the portion in the case that no crack is present in the portion based on the chosen stress-strain property to perform a numerical analysis based on the $\Delta\sigma(0)$, and wherein:

by the information processing device the growth of the crack in the portion is predicted according to the acquired stress distribution $\Delta\sigma(a)$ and the following equations:

$$da/dN = C \times (\Delta K)^m, \text{ and}$$

$$\Delta K = \Delta\sigma(a) \times (\pi \times a)^{1/2}$$

wherein "a" is a crack depth, N is a number of occurrences of a cyclic stress, C and in are constants determined for a member, and $\Delta K$ is a stress intensity factor range.

14. An information processing device comprising:

a central processing unit (CPU);

a memory that stores, for each portion on a member, stress distribution $\Delta\sigma(a)$ in the depth direction obtained in the case no crack is present, a first relationship between depth of growing cracks and creep contribution, and a second relationship between creep contribution and parameters C and m of the Paris's law; and a receiver that receives, from a user, an indication of a certain portion on the member and outputs the certain portion to the CPU, wherein the CPU determines the stress distribution $\Delta\sigma(a)$ in the depth direction for the certain portion, wherein the CPU acquires the first relationship for the certain portion from the memory and determines a creep contribution at the depth of a growing crack for the certain portion, based on the first relationship, wherein the CPU acquires the second relationship for the certain portion from the memory and determines parameters C and m corresponding to the determined creep contribution based on the second relationship, wherein the CPU predicts the growth of the crack in the certain portion, based on the following equations:

$$da/dN = C \times (\Delta K)^m, \text{ and}$$

$$\Delta K = \Delta\sigma(a) \times (\pi \times a)^{1/2}, \text{ and}$$

wherein the CPU causes a display to display the predicted growth of the crack, and wherein "a" is a crack depth, N is a number of occurrences of a cyclic stress, C and m are constants determined for a member, and $\Delta K$ is a stress intensity factor range.

15. The information processing device according to claim 14, wherein the CPU obtains the stress distribution $\Delta\sigma(a)$ in the depth direction obtained in the case no crack is present for each portion on the member by:

choosing, among known stress-strain properties, a property that satisfies the following equations:

$$1/N_f = 1/N_{pp} + 1/N_{cp},$$

$$\Delta\varepsilon_{cp} = A2 \times N_{cp}^{-\alpha 2}, \text{ and}$$

$$\Delta\varepsilon_{pp} = A1 \times N_{pp}^{-\alpha 1}$$

wherein $N_f$ is a known number of occurrences of cracks in the portion, $N_{cp}$ is a number of occurrences of cracks of a cp type (tensile creep strain+compressive plasticity strain) in strain range partitioning, $N_{pp}$ is a number of occurrences of cracks of a pp type (tensile plasticity strain+compressive plasticity strain) in the strain range partitioning, $\Delta\varepsilon_{cp}$ is a cp strain range in the strain range partitioning, $\Delta\varepsilon_{pp}$ is a pp strain range in the strain range partitioning, and A1, A2, $\alpha$1, and $\alpha$2 are all experimentally calculated constants, wherein the CPU determines stress distribution $\Delta\sigma(0)$ of the portion in the case no crack is present in the portion based on the chosen stress-strain property to perform a numerical analysis based on the $\Delta\sigma(0)$, wherein the CPU predicts the growth of the crack in the portion according to the acquired stress distribution $\Delta\sigma(a)$ and the following equations (Paris's law):

$$da/dN = C \times (\Delta K)^m, \text{ and}$$

$$\Delta K = \Delta\sigma(a) \times (\pi \times a)^{1/2}, \text{ and}$$

wherein "a" is a crack depth, N is a number of occurrences of a cyclic stress, C and m are constants determined for a member, and $\Delta K$ is a stress intensity factor range.

16. The information processing device according to claim 14, wherein the CPU corrects a curve representing a third relationship between number N of the cyclic stresses and a length "a" of a crack, when the curve has a steeply changing segment where the length "a" of the crack steeply changes relative to the change in the number N of the cyclic stresses, the curve is corrected by drawing a tangent line on an upwardly convex portion of the steeply changing segment from the vicinity of the origin, and wherein the curve is obtained by predicting growth of cracks in the certain portion.

17. The information processing device according to claim 16, wherein the CPU obtains the stress distribution $\Delta\sigma(a)$ in the depth direction obtained in the case no crack is present for each portion on the member by:

choosing, among known stress-strain properties, a property that satisfies the following equations:

$$1/N_f = 1/N_{pp} + 1/N_{cp},$$

$$\Delta\varepsilon_{cp} = A2 \times N_{cp}^{-\alpha 2}, \text{ and}$$

$$\Delta\varepsilon_{pp} = A1 \times N_{pp}^{-\alpha 1}$$

wherein $N_f$ is a known number of occurrences of cracks in the portion, $N_{cp}$ is a number of occurrences of cracks of a cp type (tensile creep strain+compressive plasticity strain) in strain range partitioning, $N_{pp}$ is a number of occurrences of cracks of a pp type (tensile plasticity strain+compressive plasticity strain) in the strain range partitioning, $\Delta\varepsilon_{cp}$ is a cp strain range in the strain range partitioning, $\Delta\varepsilon_{pp}$ is a pp strain range in the strain range partitioning, and A1, A2, $\alpha$1, and $\alpha$2 are all experimentally calculated constants, wherein the CPU determines stress distribution $\Delta\sigma(0)$ of the portion in the case no crack is present in the portion based on the chosen stress-strain property to perform a numerical analysis based on the $\Delta\sigma(0)$, wherein the CPU predicts the growth of the crack in the portion according to the acquired stress distribution $\Delta\sigma(a)$ and the following equations (Paris's law):

$$da/dN = C \times (\Delta K)^m, \text{ and}$$

$$\Delta K = \Delta\sigma(a) \times (\pi \times a)^{1/2}, \text{ and}$$

wherein "a" is a crack depth, N is a number of occurrences of a cyclic stress, C and in are constants determined for a member, and $\Delta K$ is a stress intensity factor range.

18. The information processing device according to claim 14, wherein the first relationship is calculated based on temporal change of stress at a depth of a growing crack in the member, a creep rupture property, a measured value of a number of occurrences of a cyclic stress before a crack occurs in a portion.

19. The information processing device according to claim 18, wherein the receiver receives, from the user, a length of the crack appeared on a surface of the certain portion, wherein the CPU predicts a depth of the crack occurred in the certain portion based on the length of the crack, and the predicted depth of the crack is defined as an initial value to be used in predicting a growth of a crack in the certain portion.

20. The information processing device according to claim 19, wherein the CPU determines a value obtained by multiplying the acquired length of the crack appeared on the surface of the certain portion with ⅓ as a predicted value for the depth of the crack occurred in the certain portion.

21. The information processing device according to claim 14, wherein the receiver receives, from the user, a length of the crack appeared on a surface of the certain portion, wherein the CPU predicts a depth of the crack occurred in the certain portion based on the length of the crack, and the predicted depth of the crack is defined as an initial value to be used in predicting a growth of a crack in the certain portion.

22. The information processing device according to claim 21, wherein the CPU obtains the stress distribution $\Delta\sigma(a)$ in the depth direction obtained in the case no crack is present for each portion on the member by:

choosing, among known stress-strain properties, a property that satisfies the following equations:

$$1/N_f = 1/N_{pp} + 1/N_{cp},$$

$$\Delta\varepsilon_{cp} = A2 \times N_{cp}^{-\alpha 2}, \text{ and}$$

$$\Delta\varepsilon_{pp} = A1 \times N_{pp}^{-\alpha 1}$$

wherein $N_f$ is a known number of occurrences of cracks in the portion, $N_{cp}$ is a number of occurrences of cracks of a cp type (tensile creep strain+compressive plasticity strain) in strain range partitioning, $N_{pp}$ is a number of occurrences of cracks of a pp type (tensile plasticity strain+compressive plasticity strain) in the strain range partitioning, $\Delta\varepsilon_{cp}$ is a cp strain range in the strain range partitioning, $\Delta\varepsilon_{pp}$ is a pp strain range in the strain range partitioning, and A1, A2, α1, and α2 are all experimentally calculated constants, wherein the CPU determines stress distribution $\Delta\sigma(0)$ of the portion in the case no crack is present in the portion based on the chosen stress-strain property to perform a numerical analysis based on the $\Delta\sigma(0)$, wherein the CPU predicts the growth of the crack in the portion according to the acquired stress distribution $\Delta\sigma(a)$ and the following equations (Paris's law):

$$da/dN = C \times (\Delta K)^m, \text{ and}$$

$$\Delta K = \Delta\sigma(a) \times (\pi \times a)^{1/2}, \text{ and}$$

wherein "a" is a crack depth, N is a number of occurrences of a cyclic stress, C and m are constants determined for a member, and $\Delta K$ is a stress intensity factor range.

23. The information processing device according to claim 21,
wherein the CPU corrects a curve representing a third relationship between number N of the cyclic stresses and a length "a" of a crack when the curve has a steeply changing segment where the length "a" of the crack steeply changes relative to the change in the number N of the cyclic stresses, the curve is corrected by drawing a tangent line on an upwardly convex portion of the steeply changing segment from the vicinity of the origin, and
wherein the curve is obtained by predicting growth of cracks in the certain portion.

24. The information processing device according to claim 21, wherein a value obtained by multiplying the acquired length of the crack appeared on the surface of the certain portion with ⅓ is used as a predicted value for the depth of the crack occurred in the certain portion.

* * * * *